(12) United States Patent
Luckemeyer et al.

(10) Patent No.: US 10,004,643 B2
(45) Date of Patent: Jun. 26, 2018

(54) SYNTHETIC GRANULATING GAUZE FOR USE WITH REDUCED-PRESSURE TREATMENT SYSTEMS

(71) Applicant: KCI Licensing, Inc., San Antonio, TX (US)

(72) Inventors: James Luckemeyer, San Antonio, TX (US); Timothy Mark Robinson, Basingstoke (GB); Christopher Brian Locke, Bournemouth (GB)

(73) Assignee: KCI Licensing, Inc., San Antonio, TX (US)

(*) Notice: Subject to any disclaimer, the term of this patent is extended or adjusted under 35 U.S.C. 154(b) by 690 days.

(21) Appl. No.: 13/708,759

(22) Filed: Dec. 7, 2012

(65) Prior Publication Data

US 2013/0150815 A1   Jun. 13, 2013

Related U.S. Application Data

(60) Provisional application No. 61/567,998, filed on Dec. 7, 2011.

(51) Int. Cl.
*A61M 1/00*   (2006.01)
*A61F 13/00*   (2006.01)
*A61F 13/02*   (2006.01)

(52) U.S. Cl.
CPC .. *A61F 13/00068* (2013.01); *A61F 13/00017* (2013.01); *A61F 13/00991* (2013.01); *A61F 13/0216* (2013.01); *A61M 1/0023* (2013.01); *A61M 1/0088* (2013.01)

(58) Field of Classification Search
CPC .. A61F 2013/00536; A61F 2013/00531; A61F 13/0216; A61F 13/0206; A61F 13/00991; A61F 13/00017; A61F 13/00068; A61F 2013/0054; A61M 1/0023; A61M 1/0088; A61M 27/00
See application file for complete search history.

(56) References Cited

U.S. PATENT DOCUMENTS

| | | |
|---|---|---|
| 1,355,846 A | 10/1920 | Rannells |
| 2,547,758 A | 4/1951 | Keeling |
| 2,632,443 A | 3/1953 | Lesher |
| 2,682,873 A | 7/1954 | Evans et al. |
| 2,910,763 A | 11/1959 | Lauterbach |

(Continued)

FOREIGN PATENT DOCUMENTS

| | | |
|---|---|---|
| AU | 550575 A1 | 3/1986 |
| AU | 745271 | 4/1999 |

(Continued)

OTHER PUBLICATIONS

Dictionary.com definition of gauze, http://dictionary.reference.com/browse/gauze, captured on Aug. 25, 2010, accessed on Oct. 12, 2015.*

(Continued)

*Primary Examiner* — Ariana Zimbouski

(57) ABSTRACT

A manifold member for use in applying reduced pressure to a tissue site on a patient looks or feels like medical cotton gauze but has a plurality of plurality of interlocking synthetic fibers and a plurality of asperities that provide enhanced performance. Other manifold members, systems, and methods are disclosed.

30 Claims, 4 Drawing Sheets

(56) References Cited

U.S. PATENT DOCUMENTS

| | | |
|---|---|---|
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielson |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt et al. |
| 4,941,882 A | 7/1990 | Ward et al. |
| 4,953,565 A | 9/1990 | Tachibana et al. |
| 4,969,880 A | 11/1990 | Zamierowski |
| 4,984,570 A * | 1/1991 | Langen .............. A61F 13/00008 602/44 |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,274,074 A * | 12/1993 | Tang ....................... A61L 15/64 442/301 |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,547,541 A * | 8/1996 | Hansen ............... A61F 13/0203 162/12 |
| 5,549,584 A | 8/1996 | Gross |
| 5,556,375 A | 9/1996 | Ewall |
| 5,607,388 A | 3/1997 | Ewall |
| 5,607,743 A | 3/1997 | Disselbeck |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2007/0060856 A1* | 3/2007 | Spearman ........... A61F 13/0203 602/48 |
| 2007/0185463 A1 | 8/2007 | Mulligan |
| 2007/0275073 A1* | 11/2007 | Huey ..................... A61L 15/18 424/489 |
| 2010/0055158 A1* | 3/2010 | Vitaris ................ A61F 13/0253 514/1.1 |
| 2010/0150991 A1* | 6/2010 | Bernstein ............... A61K 31/00 424/447 |
| 2010/0160876 A1* | 6/2010 | Robinson et al. ............. 604/319 |
| 2011/0224631 A1 | 9/2011 | Simmons et al. |
| 2012/0116334 A1* | 5/2012 | Albert et al. ................. 604/319 |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |
| GB | 2 333 965 A | 8/1999 |
| JP | S6060176 A | 4/1985 |
| JP | 4129536 | 4/1992 |
| JP | 2001224643 A | 8/2001 |
| JP | 2004357862 A | 12/2004 |
| JP | 5046974 B2 | 10/2012 |
| SG | 71559 | 4/2002 |
| WO | 80/02182 | 10/1980 |
| WO | 87/04626 | 8/1987 |
| WO | 90/010424 | 9/1990 |
| WO | 93/09727 | 5/1993 |
| WO | 94/020041 | 9/1994 |
| WO | 96/05873 | 2/1996 |
| WO | 97/18007 | 5/1997 |
| WO | 99/13793 | 3/1999 |

(56) References Cited

FOREIGN PATENT DOCUMENTS

WO 2010033574 A1 3/2010
WO WO 2012/078556 A2 6/2012

OTHER PUBLICATIONS

Asperity, Merriam-Webster, http://www.merriam-webster.com/dictionary/asperity, published Apr. 10, 2010, accessed Feb. 13, 2017.*
N. A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96 (certified translation).
Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.
Susan Mendez-Eastmen, RN; "When Wounds Won't Heal" RN Jan. 1998, vol. 61 (1); Medical Economics Company, Inc., Montvale, NJ, USA; pp. 20-24.
James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), vol. 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & dated Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, p. 1.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., vol. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovic, V. Ðukić, Ž. Maksimovíc, Ð. Radak, and P. Peš ka, "Vacuum Therapy in the Treatment of Peripheral Blood Vessels," Timok Medical Journal 11 (1986), pp. 161-164 (certified translation).
F.E. E Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, "An Improved Sump Drain-Irrigation Device of Simple Construction," Archives of Surgery 105 (1972) pp. 511-513.
C.E. Tennant, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians (Jul. 2007).
International Search Report and Written Opinion for corresponding PCT/US2012/068583, dated Feb. 11, 2013.
Japanese Notice of Rejection corresponding to Application No. 2014546146, dated Oct. 10, 2017.

* cited by examiner

SYNTHETIC GRANULATING GAUZE FOR USE WITH REDUCED-PRESSURE TREATMENT SYSTEMS

CROSS-REFERENCE TO RELATED APPLICATION

This application claims priority to U.S. Provisional Patent Application No. 61/567,998 filed Dec. 7, 2011, entitled SYNTHETIC GRANULATING GAUZE FOR USE WITH REDUCED-PRESSURE TREATMENT SYSTEMS, the disclosure of which is hereby incorporated by reference in its entirety.

BACKGROUND OF THE INVENTION

1. Field of the Invention

The present disclosure relates generally to medical treatment systems for treating wounds, and more particularly, but not by way of limitation, to synthetic granulating gauze for use with reduced-pressure treatment systems, reduced-pressure systems, and methods.

2. Description of Related Art

Clinical studies and practice have shown that providing reduced pressure in proximity to a tissue site augments and accelerates the growth of new tissue at the tissue site The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, which may include faster healing and increased formulation of granulation tissue. In applying reduced-pressure therapy, typically, a foam pad is placed proximate to the wound, covered with a drape, and reduced pressure applied.

SUMMARY

According to an illustrative embodiment, a manifold member for use in a reduced-pressure treatment system includes a plurality of interlocking synthetic fibers forming a pad having a first side and a second side. The manifold member further includes a plurality of asperities formed on at least the first or second side of the pad. The plurality of asperities promote granulation tissue at the tissue site.

According to another illustrative embodiment, a system for treating a tissue site on a patient with reduced pressure includes a manifold member adapted to be disposed proximate to the tissue site, a sealing member adapted to cover the manifold member and form a sealed space, and a reduced-pressure source fluidly coupled to the sealed space. The manifold member includes a plurality of interlocking synthetic fibers forming a pad having a first side and a second side. The manifold member further includes a plurality of asperities formed on at least the first or second side of the pad.

According to another illustrative embodiment, a method of manufacturing a manifold member for use in a reduced-pressure treatment system to treat a tissue site includes forming a plurality of synthetic fibers, forming a pad from the plurality of synthetic fibers having a first side and a second side, and coupling a plurality of asperities on at least a portion of the pad. The plurality of asperities may be coupled by bonding or may be molded as an aspect of the plurality of synthetic fibers.

According to another illustrative embodiment, a manifold member for use in a reduced-pressure treatment system includes a layer of open-cell foam having a first side and a second side. The manifold member also includes a plurality of interlocking fibers coupled to the layer of open-cell foam.

Other aspects, features, and advantages of the illustrative embodiments will become apparent with reference to the drawings and detailed description that follow.

DETAILED DESCRIPTION OF ILLUSTRATIVE EMBODIMENTS

In the following detailed description of illustrative, non-limiting embodiments, reference is made to the accompanying drawings that form a part hereof. These embodiments are described in sufficient detail to enable those skilled in the art to practice the invention, and it is understood that other embodiments may be utilized and that logical, structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is not to be taken in a limiting sense, and the scope of the illustrative embodiments are defined only by the appended claims.

Figure 1:
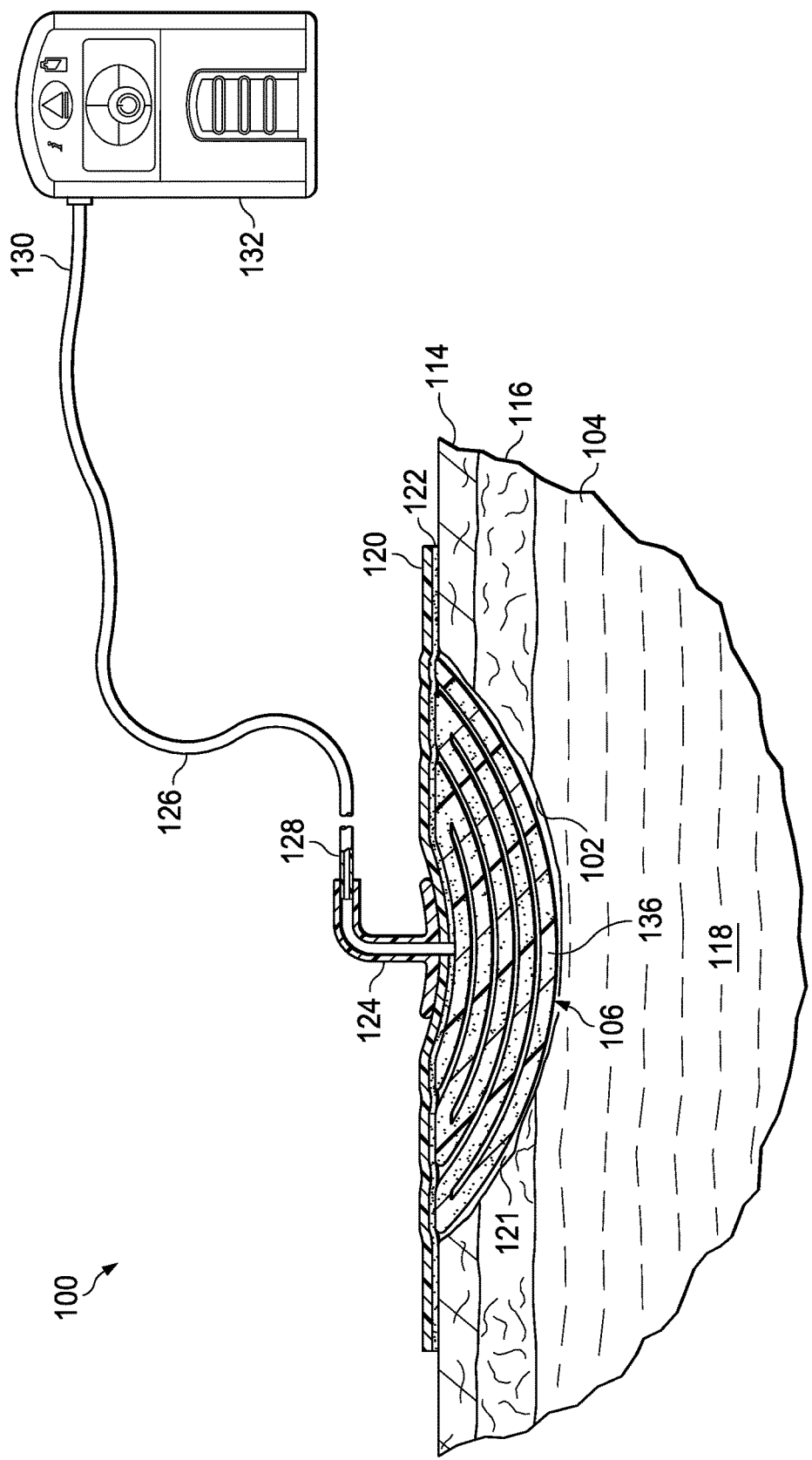
FIG. 1 is a schematic, cross-sectional view of an illustrative embodiment of a system for treating a tissue site on a patient with reduced pressure that includes an illustrative embodiment of a manifold member.

Referring now to the figures, and initially to FIG. 1, an illustrative embodiment of a system 100 for treating a tissue site 102 on a patient 104 with reduced pressure is presented. The system 100 includes an illustrative embodiment of a manifold member 106 formed with a plurality of synthetic fibers 108 and a plurality of asperities 110 (see, e.g., asperities 110 in FIG. 2). The manifold member 106 may be synthetic, but adapted to have the look or feel of medical cotton gauze. The manifold member 106 includes asperities 110. The asperities 110 may enhance the granulation of the tissue site 102 or provide flow pathways to facilitate reduced-pressure manifolding. As used throughout this document, "or" does not require mutual exclusivity. Because the plurality of asperities 110 enhance granulation, the manifold member 106 may be referred to as a synthetic granulating gauze. The manifold member 106 is described in more detail further below.

The tissue site 102 may be the bodily tissue of any human, animal, or other organism, including bone tissue, adipose tissue, muscle tissue, dermal tissue, vascular tissue, connective tissue, cartilage, tendons, ligaments, or any other tissue. Treatment of the tissue site 102 may include reduced-pressure therapy to promote granulation or removal of fluids, e.g., exudate or ascites. In the illustrative example of FIG. 1, the tissue site 102 is a wound on the patient 104. The wound extends through epidermis 114, through dermis 116, and into subcutaneous tissue 118.

The manifold member 106 is disposed proximate to the tissue site 102 and is covered by a sealing member 120 to form a sealed space 121. The sealing member 120 may be any material that provides a fluid seal. A fluid seal is a seal adequate to maintain reduced pressure at a desired site given the particular reduced-pressure source or subsystem involved. The sealing member 120 may be, for example, an impermeable or semi-permeable, elastomeric material. For semi-permeable materials, the permeability must be low enough that for a given reduced-pressure source, the desired reduced pressure may be maintained.

An attachment device 122 may be used to hold the sealing member 120 against the patient's epidermis 114 or another layer, such as a gasket or additional sealing member. The attachment device 122 may take numerous forms. For example, the attachment device 122 may be a medically acceptable, pressure-sensitive adhesive that extends about a periphery, a portion, or the entire sealing member 120; a double-sided drape tape; paste; hydrocolloid; hydro-gel; silicone gel; organogel; or other sealing device or elements.

A reduced-pressure interface 124 is applied to the sealing member 120 to provide fluid communication to the sealed space 121. The reduced-pressure interface 124 may be any device that provides such fluid communication or a fluid coupling. In one illustrative embodiment, the reduced-pressure interface 124 is a T.R.A.C.® Pad or Sensa T.R.A.C.® Pad available from KCI of San Antonio, Tex. In one illustrative embodiment, the reduced-pressure interface 124 may be a portion of a conduit extending through the sealing member 120.

A reduced-pressure delivery conduit 126 is fluidly coupled at a first end 128 to the reduced-pressure interface 124. A second end 130 of the reduced-pressure delivery conduit 126 is fluidly coupled to a reduced-pressure source 132. The reduced-pressure delivery conduit 126 is typically a medical tube or other means of conveying fluids.

The reduced-pressure source 132 may be any device for supplying a reduced pressure, such as a vacuum pump, wall suction, micro-pump, or other source. While the amount and nature of reduced pressure applied to a tissue site will typically vary according to the application, the reduced pressure will typically be between −5 mm Hg (−667 Pa) and −500 mm Hg (−66.7 kPa) and more typically between −75 mm Hg (−9.9 kPa) and −300 mm Hg (−39.9 kPa).

Reduced pressure is typically a pressure less than the ambient pressure at a tissue site that is being subjected to treatment. In most cases, this reduced pressure will be less than the atmospheric pressure at which the patient 104 is located. Alternatively, the reduced pressure may be less than a hydrostatic pressure at the tissue site 102. Unless otherwise indicated, quantitative values of pressure stated herein are gauge pressures. The reduced pressure delivered may be constant or varied (patterned or random) and may be delivered continuously or intermittently. Although the terms "vacuum" and "negative pressure" may be used to describe the pressure applied to the tissue site, the actual pressure applied to the tissue site may be more than the pressure normally associated with a complete vacuum. Consistent with the use herein, unless otherwise indicated, an increase in reduced pressure or vacuum pressure typically refers to a reduction in absolute pressure.

Referring now primarily to FIGS. 1-5, the manifold member 106 is typically formed to look or feel like medical cotton gauze. The look or feel of medical cotton gauze is a characteristic some healthcare professionals desire. While looking or feeling like medical cotton gauze, the manifold member 106 provides improved performance with respect to reduced-pressure treatments. The manifold member 106 is disposed in the wound bed or against the tissue site 102 as any gauze might be, and yet, the performance of the manifold member 106 is enhanced.

The manifold member 106 may be formed with a plurality of synthetic fibers 108. The synthetic fibers 108 can be woven or combined to form a plurality of interlocking synthetic fibers 134 that form a porous pad, such as pad 136. The pores in pad 136 provide flow channels or pathways through pad 136, which are adapted to distribute reduced pressure to a tissue site The pad 136 has a first side 138 and a second side 140. The plurality of asperities 110 may be formed on one or both of the sides 138, 140 of the pad 136 and may be attached to or formed as part of the plurality of synthetic fibers 108.

The plurality of synthetic fibers 108 may be formed, for example, from one or more of the following: non-woven rayon, rayon with a cellulose formulation, polyesters, polyamides, polyolefins, poly acrylics, polyvinyl acetates, polyvinyl alcohols and copolymers, polyurethanes, or other polymers. The synthetic fibers 108 may have a circular cross section or an irregular cross section (e.g., lobed), for example. The plurality of synthetic fibers 108 may be formed by spin-forming or blow-forming processes to mimic the look or feel of natural cotton. The synthetic fibers 108 may be formed to be hydrophilic or hydrophobic. A pigment may be added to the material forming the synthetic fibers 108. In one illustrative embodiment, the synthetic fibers 108 are formed from fibers with an effective diameter less than 20 microns, though coarser meshes could also be used, where the fiber diameter is about 200 microns or any dimension between. An effective average diameter for the plurality of interlocking synthetic fibers 108 is typically greater than 15 microns and less than 25 microns. A range of densities for the pad 136 are possible from about 20 grams per square meter (gsm) to about 200 gsm. Compression stiffness of the manifold member 106 would be greater than medical cotton gauze and may be in the range of 8 kPa at 50% compression. The synthetic fibers 108 are combined to form the plurality of interlocking synthetic fibers 134 that form the pad 136.

Numerous materials may be added to the plurality of synthetic fibers 108. For example, a pigment of any of numerous colors may be included in the plurality of synthetic fibers 108 to allow easy visual recognition. Antimicrobials (e.g., silver) may be added to the plurality of synthetic fibers 108. As still another example, a radiopaque material may be added to the plurality of synthetic fibers 108. In the latter example, radiography may be used to locate any radiopaque material left in a wound bed after a dressing change. As yet another example, a stiffening material, e.g., a starch or water-sensitive polymer such as polyvinyl alcohol, may be added that provides relatively greater stiffness to the manifold member 106 and that decreases in stiffness when the stiffening material becomes wet.

The plurality of asperities 110 may enhance granulation by providing micro-strain or relatively more micro-strain on the tissue site 102. The plurality of asperities 110 also helps provide flow paths through the manifold member 106. The plurality of asperities 110 may be molded or bonded or otherwise formed on the pad 136 or plurality of synthetic fibers 110. The plurality of asperities 110 may be formed from a polymer such as polyurethane, silicone, TPE, polyether block polyamide (PEBAX), or polyolefin elastomers, for example. The plurality of asperities 110 may have a stiffness of 40 to 60 Shore A durometer. The plurality of asperities 110 has an average volume of about 0.125 mm$^3$ to about 8 mm$^3$.

An asperity 110 may comprise a polymer particle or nodule having at least one dimension longer than 10 microns. The plurality of asperities 110 may have a pigment added or other additives such as antimicrobials. The plurality of asperities 110 may be formed in any shape as a nodule, e.g., irregular, dome, square, rectangular, triangular, or other shape. The plurality of asperities 110 may be any surface irregularity that creates gaps and features. The shape of the plurality of asperities 110 may limit or prohibit in-growth into the structure to facilitate removing the manifold member 106 at a dressing change.

Figure 2:
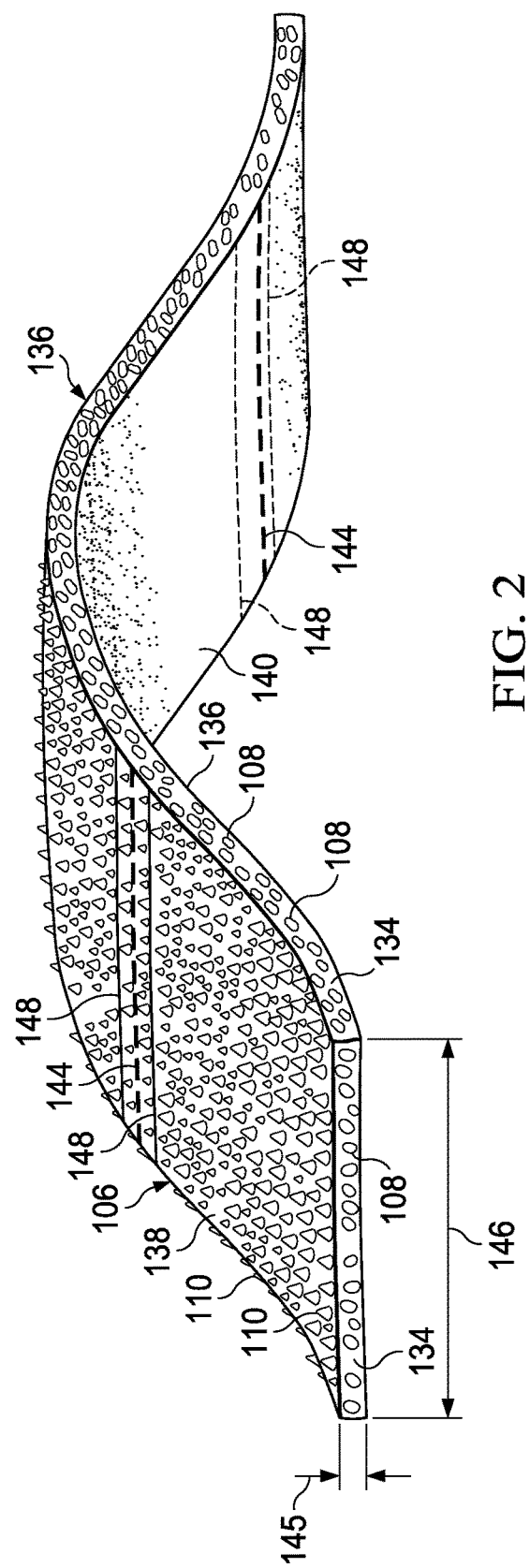
FIG. 2 is a schematic perspective view (with a portion in cross section) of an illustrative embodiment of a manifold member forming a pad.

The synthetic fibers 108 and asperities 110 may be formed in numerous ways. Referring now primarily to FIG. 2, in one embodiment, the plurality of asperities 110 are coupled to the pad 136. For example, the plurality of asperities 110 may be bonded to the pad 136. The bond may be formed using a non-water-soluble adherent coating process, e.g., acrylic, polyurethane, silicon or an elastomeric based medical grade adhesive. The bonds may also be formed using a heat bond or flame lamination.

In one illustrative embodiment, the plurality of synthetic fibers 108, which form the pad 136, and the plurality of asperities 110 may be formed by forming a polymer fiber mat and then sputter-coating features or objects onto the surface of the polymer fiber mat. The asperities 110 may be formed from another polymer or any other suitable material with suitable bonding properties. In another illustrative embodiment, the plurality of asperities 110 comprise starch that can be safely left in the wound. The asperities 110 may be tagged for subsequent imaging.

The manifold member 106 may be formed as a longitudinal strip that has perforations or tear paths 144. The finished manifold member 106 may be rolled onto a reel or provided in strip form for the end user. The thickness 145 of the manifold member 106 is typically in the range of about 1 mm to about 5 mm, and the width 146 is typically in the range of about 1 cm to about 30 cm. It will be appreciated that other dimensions are possible.

Figure 3:
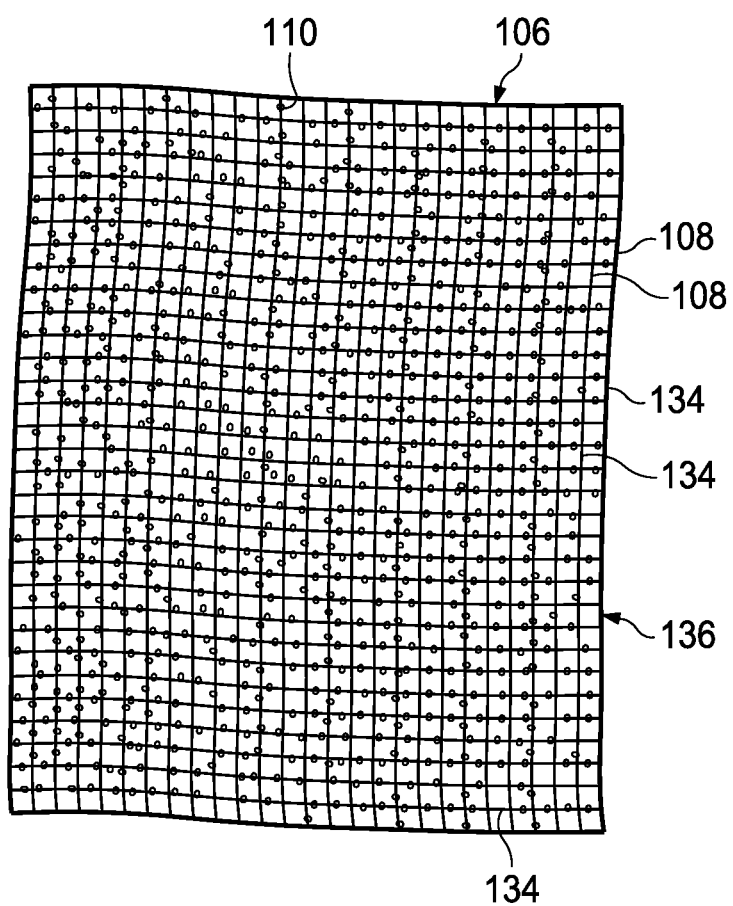
FIG. 3 is a schematic plan view of an illustrative embodiment of a manifold member forming a pad.
Figure 4:
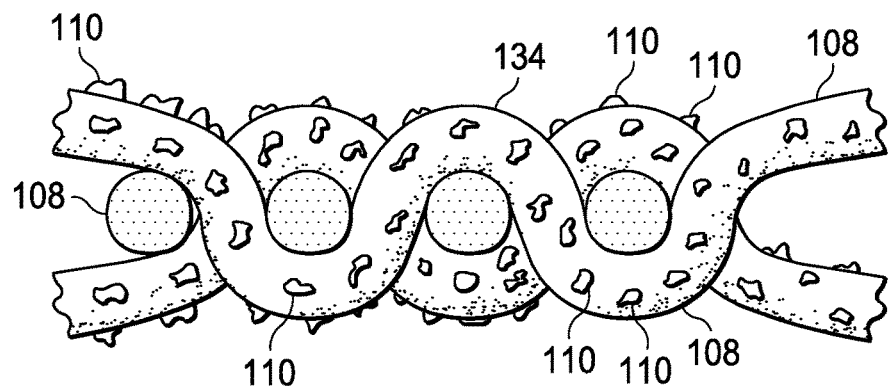
FIG. 4 is a schematic cross-sectional view of the manifold member of FIG. 3.

Referring now primarily to FIGS. 3 and 4, in another illustrative embodiment, the plurality of asperities 110 are formed on the plurality of synthetic fibers 108 themselves. For example, the plurality of synthetic fibers 108 and the plurality of asperities 110 may be formed by molding, extruding, calendering, printing, spraying, or other means.

Figure 5:
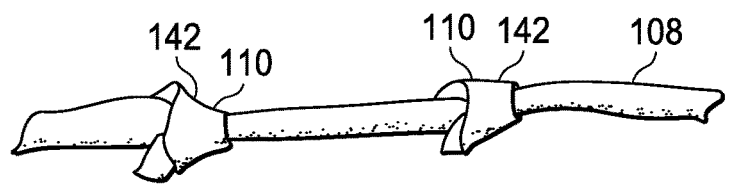
FIG. 5 is a schematic elevation view of a synthetic fiber formed with a plurality of knots.

Referring now primarily to FIG. 5, in another illustrative embodiment, the plurality of synthetic fibers 108 are formed with a plurality of knots 142 or knot-like structures formed longitudinally along each synthetic fiber 108. The synthetic fibers 108 are woven, knitted, braided, dry-laid, meltblown, formed with techniques and methods used in lace making and net making, or otherwise interlocked to form the plurality of interlocked synthetic fibers 134 that form the pad 136.

With the various ways of forming the manifold member 106, it should be noted that the mechanical properties of the manifold member 106 may be controlled by the choice of the polymer or polymer blend, cross-section (e.g., formed fiber cross-section with sharp edges or smooth circles), and fiber-strand geometry (minimize spring back). For example, small diameter fibers may be used in some situations because smaller diameter fibers tend to form softer compliant structures compared with structures formed from larger diameter fibers. Lobed and longitudinally grooved fibers may be used to enhance the wicking behavior of the manifold member 106.

The manifold member 106 may be formed as sheets of material—sheets comprising the plurality of interlocking synthetic fibers 134 and plurality of asperities 110. Additional layers may be laminated onto the pad 136 for different applications. For example, hydrogels, silicone gels, perforated films, and antimicrobial layers may be laminated onto the pad 136.

Referring again primarily to FIG. 2, but applicable to other embodiments, the pad 136 may be perforated or partially cut to form a tear path 144 to facilitate tearing. The pad 136 is typically placed on a roll. The tear paths 144 are displaced longitudinally and extend laterally across the width 146. The tear paths 144 may be formed from solid perforations, or from segment perforations or kiss-cuts to control the tear path. A containment bond 148 may be formed on each side of each tear path 144 to keep the fibers 108 together along the tear path 144 after tearing. The manifold member 106 may be configured not to separate by hand unless torn along a tear path 144 or cut with a cutting tool.

With respect to all embodiments, the manifold member 106 may be flocked or coated with another fine fiber material to increase the softness or bulk of the manifold member 106. The flock may impart hydrophobic or hydrophilic character to the manifold member 106. The fine fiber may also be formed from a super-absorbent polymer that gels when liquids are absorbed. Examples of fine fibers include polyesters, polyamides, polyacrylics, polyvinyl alcohols and copolymers fibers.

Referring now primarily to FIGS. 1-5, in operation according to one illustrative embodiment, the user sizes the manifold member 106 by selecting a strip of the manifold member 106 that may be turned on itself or packed as shown in FIG. 1, or an appropriate tear path 144 may be torn or cut to provide one or more pieces of the manifold member 106 to adequately cover the tissue site 102. The manifold member 106 may be substantially applied to the tissue site 102 like medical cotton gauze, except that tear paths 144 or a cutting tool may be used instead of mere ripping.

After deploying the manifold member 106, the tissue site 102 may be covered with the sealing member 120. The reduced-pressure interface 124 is applied to provide fluid communication to the sealed space 121 that contains the manifold member 106. The reduced-pressure interface 124 is fluidly coupled by the reduced-pressure delivery conduit 126 to the reduced-pressure source 132. Alternatively, a micro-pump (not explicitly shown) may be applied directly on the sealing member 120 with an aperture for providing fluid access to the sealed space 121. The reduced-pressure source 132 is activated and reduced pressure may be distributed through the manifold member 106 to the tissue site 102.

The manifold member 106 may be quickly disposed in the wound. The manifold member 106 may provide the look or feel of cotton gauze, but can provide hydrophobic manifolding for reduced pressure rather than hydrophilic absorption. The manifold member 106 may also offer improved granulation or fluid flow when used with negative pressure wound therapy.

Figure 6:
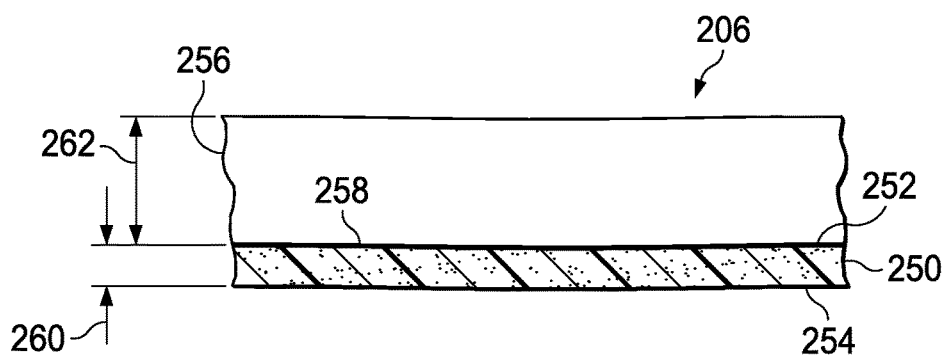
FIG. 6 is a schematic cross-sectional view of an illustrative embodiment of a manifold member.

Referring now primarily to FIG. 6, an alternative embodiment of an illustrative manifold member 206 for use in a reduced-pressure system (see 100 in FIG. 1) is presented. The manifold member 206 includes a layer of open-cell foam 250 having a first side 252 and a second side 254. The manifold member 206 further includes a plurality of interlocking fibers 256. The interlocking fibers 256 may be formed from a synthetic material, e.g., a polymer, or cellulose fibers. In one illustrative example, the open-cell foam 250 may be applied to one side of a medical cotton gauze. The plurality of interlocking fibers 256 is coupled to the layer of open-cell foam 250 by a bond 258. The bond 258 may be an adhesive, weld, mechanical interlocking, or other attachment means. The layer of open-cell foam 250 has a thickness 260 less than 3 millimeters and the plurality of interlocking fibers 256 has a thickness 262 less than 3 millimeters. In use, the open-cell foam 250 is deployed adjacent to the tissue site and used as described in connection with FIG. 1.

Although the present invention and its advantages have been disclosed in the context of certain illustrative, non-limiting embodiments, it should be understood that various changes, substitutions, permutations, and alterations can be made without departing from the scope of the invention as defined by the appended claims. It will be appreciated that any feature that is described in connection to any one embodiment may also be applicable to any other embodiment.

It will be understood that the benefits and advantages described above may relate to one embodiment or may relate to several embodiments. It will further be understood that reference to "an" item refers to one or more of those items.

The steps of the methods described herein may be carried out in any suitable order, or simultaneously where appropriate.

Where appropriate, aspects of any of the embodiments described above may be combined with aspects of any of the other embodiments described to form further examples having comparable or different properties and addressing the same or different problems.

It will be understood that the above description of preferred embodiments is given by way of example only and that various modifications may be made by those skilled in the art. The above specification, examples and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the scope of the claims.

We claim:

1. A manifold member for treating a tissue site, the manifold member comprising:
   a plurality of synthetic fibers flocked with a plurality of softening fibers and woven to form a gauze having a first side and a second side, wherein the plurality of softening fibers comprise a material that is different from a material of the plurality of synthetic fibers; and
   a plurality of asperities formed on at least the first or second side of the gauze, wherein the plurality of asperities are configured to promote granulation tissue at the tissue site;
   wherein each of the plurality of asperities comprise molded polymer nodules having at least one dimension longer than 10 microns and being bonded to at least one of the first side or the second side of the gauze.

2. The manifold member of claim 1, wherein the gauze has a density in a range of about 20 grams per square meter (gsm) to 200 gsm.

3. The manifold member of claim 1, wherein an average diameter for the plurality of synthetic fibers is greater than 15 microns and less than 25 microns.

4. The manifold member of claim 1, wherein the plurality of asperities has an average effective diameter less than 20 microns.

5. The manifold member of claim 1, wherein each of the plurality of asperities is triangular.

6. The manifold member of claim 1, wherein the synthetic fibers are hydrophilic.

7. The manifold member of claim 1, wherein the synthetic fibers are hydrophobic.

8. The manifold member of claim 1, wherein the plurality of synthetic fibers comprise at least one of the following: polyesters, polyamides, and polyolefins.

9. The manifold member of claim 1, wherein the plurality of synthetic fibers comprise a pigment.

10. The manifold member of claim 1, wherein the plurality of synthetic fibers comprise fibers having a circular cross section.

11. The manifold member of claim 1, wherein the plurality of synthetic fibers comprise fibers having a lobed cross section.

12. The manifold member of claim 1, wherein the plurality of synthetic fibers comprise a starch or a water-sensitive polymer to provide a stiffness that is greater when dry than wet.

13. The manifold member of claim 1, wherein the plurality of synthetic fibers comprise a radiopaque marker.

14. A system for treating a tissue site with reduced pressure, the system comprising:
   a gauze having a first side and a second side and formed from a woven plurality of synthetic fibers flocked with a plurality of softening fibers, wherein the plurality of softening fibers comprise a material that is different from a material of the plurality of synthetic fibers;
   a plurality of asperities formed on at least the first or second side of the gauze, wherein each of the plurality of asperities comprise molded polymer nodules having at least one dimension longer than 10 microns and being bonded to at least one of the first side or the second side of the gauze;
   a sealing member covering the manifold member and adapted to form a sealed space around the tissue site; and
   a reduced-pressure source fluidly coupled to the gauze.

15. The system of claim 14, wherein the gauze has a density in a range of about 20 grams per square meter (gsm) to 200 gsm.

16. The system of claim 14, wherein an average diameter for the plurality of synthetic fibers is greater than 15 microns and less than 25 microns.

17. The system of claim 14, wherein the plurality of asperities have an average effective diameter less than 20 microns.

18. The system of claim 14, wherein each of the plurality of asperities is triangular.

19. The system of claim 14, wherein the synthetic fibers are hydrophilic.

20. The system of claim 14, wherein the synthetic fibers are hydrophobic.

21. The system of claim 14, wherein the plurality of synthetic fibers comprise at least one of the following: polyesters, polyamides, and polyolefins.

22. The system of claim 14, wherein the plurality of synthetic fibers comprise a pigment.

23. The system of claim 14, wherein the plurality of synthetic fibers comprise fibers having a circular cross section.

24. The system of claim 14, wherein the plurality of synthetic fibers comprise fibers having a lobed cross section.

25. The system of claim 14, wherein the plurality of synthetic fibers comprise a starch or a water-sensitive polymer to provide a stiffness that is greater when dry than wet.

26. The system of claim 14, wherein the plurality of synthetic fibers comprise a radiopaque marker.

27. A manifold for distributing reduced pressure to a tissue site, the manifold comprising:

a gauze of woven synthetic fibers flocked with softening fibers and adapted to provide flow channels through the gauze, wherein the woven softening fibers comprise a material that is different from a material of the synthetic fibers; and a plurality of asperities disposed on the gauze;

wherein the asperities have a stiffness in a range of about 40 Shore A durometer to 60 Shore A durometer and an average volume in the range of about 0.125 $mm^3$ to about 8 $mm^3$;

wherein the diameter of the synthetic fibers is in a range of about 15 microns to 20 microns; and wherein the compression stiffness of the gauze is about 8 kPa at 50 % compression.

28. The manifold of claim 27, wherein the gauze has a thickness in a range of about 1 mm to about 5 mm and a width in a range of about 1 cm to about 30 cm.

29. The manifold of claim 27, wherein the synthetic fibers are polymer fibers.

30. The manifold of claim 27, wherein the synthetic fibers are hydrophobic.

* * * * *